US005595748A

United States Patent [19]

Hewlett et al.

[11] Patent Number: 5,595,748

[45] Date of Patent: Jan. 21, 1997

[54] COMPOSITIONS AND METHODS FOR CONTROLLING NEMATODES

[76] Inventors: Eric M. Hewlett; Thomas E. Hewlett, both of 5401 NW. 23rd Pl., Gainesville, Fla. 32606

[21] Appl. No.: 394,090

[22] Filed: Feb. 24, 1995

[51] Int. Cl.$^{6}$ .......... A01N 25/12

[52] U.S. Cl. .......... 424/405; 424/409

[58] Field of Search .......... 424/405, 409; 71/6, 23

[56] References Cited

U.S. PATENT DOCUMENTS

| | | | |
|---|---|---|---|
| 2,735,858 | 2/1956 | Bergman | 71/23 |
| 3,270,003 | 8/1966 | Van Blaricom et al. | 71/23 |
| 3,473,255 | 10/1969 | Working | 71/23 |
| 3,855,121 | 12/1974 | Gough | 252/180 |
| 4,116,663 | 9/1978 | Ballou | 71/23 |
| 4,583,320 | 4/1986 | Redenbaugh | 47/57.6 |
| 4,779,376 | 10/1988 | Redenbaugh | 47/57.6 |
| 4,948,734 | 8/1990 | Edwards et al. | 435/252.5 |
| 4,985,060 | 1/1991 | Higa | 71/6 |
| 5,151,363 | 9/1992 | Payne | 435/252.5 |

OTHER PUBLICATIONS

Chalfie et al., Chemical Abstracts, vol. 96, 1983, #178408.

Balaji et al., Chemical Abstracts, vol. 109, 1989, #68369.

Ballou, World Patent Index Abstracts, 78–72404A.

Kiuchi, F. et al. (1987) "Studies on Crude Drugs Effective on Visceral Larva Migrans. I. Identification of Larvicidal Principles in Betel Nuts" Chem. Pharm Bull. 35:2880–2886.

Prichard, R. K. et al. (1980) "The problem of anthelmintic resistance in sheep" Austr. Vet. J. 56:239–251.

Coles, G. C. (1986) "Anthelmintic resistance in sheep" Veterinary Clinics of North America: Food Animal Practice 2:423–432.

*Primary Examiner*—Thurman K. Page

*Attorney, Agent, or Firm*—Saliwanchik & Saliwanchik

[57] ABSTRACT

The subject invention concerns pest-control compositions and advantageous methods of using these compositions. More specifically, this invention relates to the use of tannins (tannic acid and other analogues, congeners, derivatives, or salts of tannic acid) to control plant-parasitic nematodes. Tannins can be used as nematicides or as nematode-attractants.

9 Claims, 3 Drawing Sheets

X X X COOCH HCOH X X X COOCH HCOH HCO X X X COOCH

COMPOSITIONS AND METHODS FOR CONTROLLING NEMATODES

BACKGROUND OF THE INVENTION

Damage to plants caused by nematodes is a prevalent and serious economic problem. Nematodes cause wide-spread and serious damage in many plant species. Many genera of nematodes are known to cause such damage. Plant-parasitic nematodes include members of the Phylum Nematoda, Orders Tylenchida and Dorylaimide. In the Order Tylenchida, the plant-parasitic nematodes are found in two Super Families: Tylenchoidea and Criconematoidea. There are more than 100,000 described species of nematodes.

Nematicides routinely used for control of plant-parasitic nematodes are rapidly being pulled from the market as concern for environmental safety increases. In the year 2001, Methyl Bromide, a mainstay in the control of such parasites, will no longer be marketed in the United States. Therefore, less harmful control agents are clearly needed.

In addition, the regular use of chemical toms to control unwanted organisms can select for drug-resistant strains. This has occurred in many species of economically important insects and has also occurred in nematodes of sheep, goats, and horses. For example, an accepted methodology for control of nematodes has centered around the drug benzimidazole and its congeners. The use of these drugs on a wide scale has led to many instances of resistance among nematode populations (Prichard, R. K. et al. [1980] "The problem of anthelmintic resistance in nematodes," Austr. Vet. J. 56:239–251; Coles, G. C. [1986] "Anthelmintic resistance in sheep," In *Veterinary Clinics of North America: Food Animal Practice,* Vol 2:423–432 [Herd, R. P., eds.] W. B. Saunders, New York). The development of pesticide resistance necessitates a continuing search for new control agents having different modes of action.

As discussed in more detail below, nematodes sense the presence of and navigate toward root systems of plants. Our research has demonstrated that tannins are strong attractants of plant-parasitic nematodes. Certain aspects of the research described herein were presented at a science fair in February 1994.

Tannins are produced in the roots, stems, and leaves of almost all plants. It was known that tannins were present in the waste discharge of paper mills and nut-processing plants. See U.S. Pat. No. 3,855,121, Gough, Biochemical Process. Tannins are used, for example, to denature alcohol, to tan animal hides, as clarification agents in wine and beer manufacturing, in the production of inks, pharmaceuticals, and paper. Tannins can also be used to deodorize crude oil. Tannins are also used in the production of galvano-plastics (as a gelatin precipitant). Similarly, tannins have been used as complexing agents for gel matrices. See U.S. Pat. No. 4,779,376, Redenbaugh, *Delivery System for Seeds;* U.S. Pat. No. 4,583,320, Redenbaugh, *Delivery System for Meristematic Tissue.*

BRIEF SUMMARY OF THE INVENTION

The subject invention concerns compositions and methods for the control of plant pests. More specifically, this invention relates to the use of tannins to control plant-parasitic nematodes. An important aspect of the subject invention is the discovery that nematodes preferentially migrate towards tannins. As described herein, tannins can be used according to the subject invention in the effective control of plant-parasitic nematodes while avoiding a negative impact on the environment which can result from the normal use of synthetic chemical pesticides.

Described herein are various nematode control methodologies which exploit the discovery that nematodes migrate towards tannins. In one embodiment of the subject invention, a composition comprising tannins and an inert carrier or solvent is placed in soil at a location away from the root system of plants. Nematodes present in the soil can detect the tannins and migrate toward the tannin source, and thus migrate away from the roots of a plant which is to be protected from nematode infestation.

In another embodiment of the subject invention, tannins can be combined with a second nematode control agent. In this manner, the subject invention can be used to attract nematodes to the second control agent. The second control agent used according to this embodiment of the subject invention can be any known chemical or biological nematicidal agent, or any such agent which may be developed in the future. Preferably, the nematicide is non-toxic to the environment or to humans. Examples of known control agents include pesticides based upon *Bacillus thuringiensis* (*B.t.*) isolates or products comprising *B.t.* toxins having activity against nematodes.

In yet another embodiment, the tannins can be combined with a food source for nematodes such that the nematodes which are attracted away from the plants will have a food source which will farther entice the nematode pest to remain at the location away from the desired plant.

It has also been found that in certain soft concentrations, e.g., 10,000 ppm or more, tannins can be used as nematicides. If nematicidal activity is desired it can be achieved by compositions of the subject invention having tannin concentrations in soil at more than about 50,000 ppm, and most preferably at concentrations of about 100,000 ppm or more. At lower concentrations, e.g., less than about 10,000 ppm, tannins can be used as a nemastat or nematode attractant. In this manner, applied tannins can be used to lead nematodes away from the desired plants. Thus, the numbers of nematodes that are able to locate and parasitize plant root systems are greatly reduced. Use of tannins also allows for stimulation of nematodes to move during periods when no crop is present in field situations. By inducing migrations behavior, nematodes can use up their energy stores, become weakened, and die before damaging the roots of desired plants.

The compositions of the subject invention can be formulated in various forms in order to provide an effective concentration of tannins. Such formulations include, for example, granules, water-soluble sprays, or pellets of sea weed agar or clay. Advantageously, tannins can be introduced into the soil from point sources (pellets) or by saturation (granular or liquid). As described herein, point source applications of tannins also make possible the luring of nematodes to locations having other chemical or biological control agents, such as chemical pesticides or antagonistic organisms like fungi and bacteria. Used in this manner, tannins may be used to decrease the amount of chemical or biological control agents needed to treat large field areas. Tannins can be used to control nematodes in various settings, including farmland, golf courses, green houses, in the potted-plant industry, and around the home, for example, in vegetable gardens.

DETAILED DESCRIPTION OF THE INVENTION

The subject invention concerns pest-control compositions and advantageous methods of using these compositions. More specifically, the subject invention relates to the use of tannins to control plant-parasitic nematodes. The use of tannins as an agent to control plant-parasitic nematodes can be very valuable and helps to avoid a negative impact on the environment which can result from the normal use of synthetic chemical pesticides. We have found that, unexpectedly, nematodes can detect low concentrations of tannins in soil and are attracted to (and navigate toward) these chemicals. Higher concentrations of tannins affect the ability of nematodes to migrate, i.e., tannins can alter normal search behavior exhibited by nematodes foraging for food. Still higher concentrations of tannins in the soil can completely immobilize the nematode and can be lethal to the pests. Thus, applying tannins around desirable plants can cause nematodes to inefficiently and ineffectively forage for food, which greatly reduces the number of nematodes that are able to locate and parasitize plant root systems.

Figure 1:
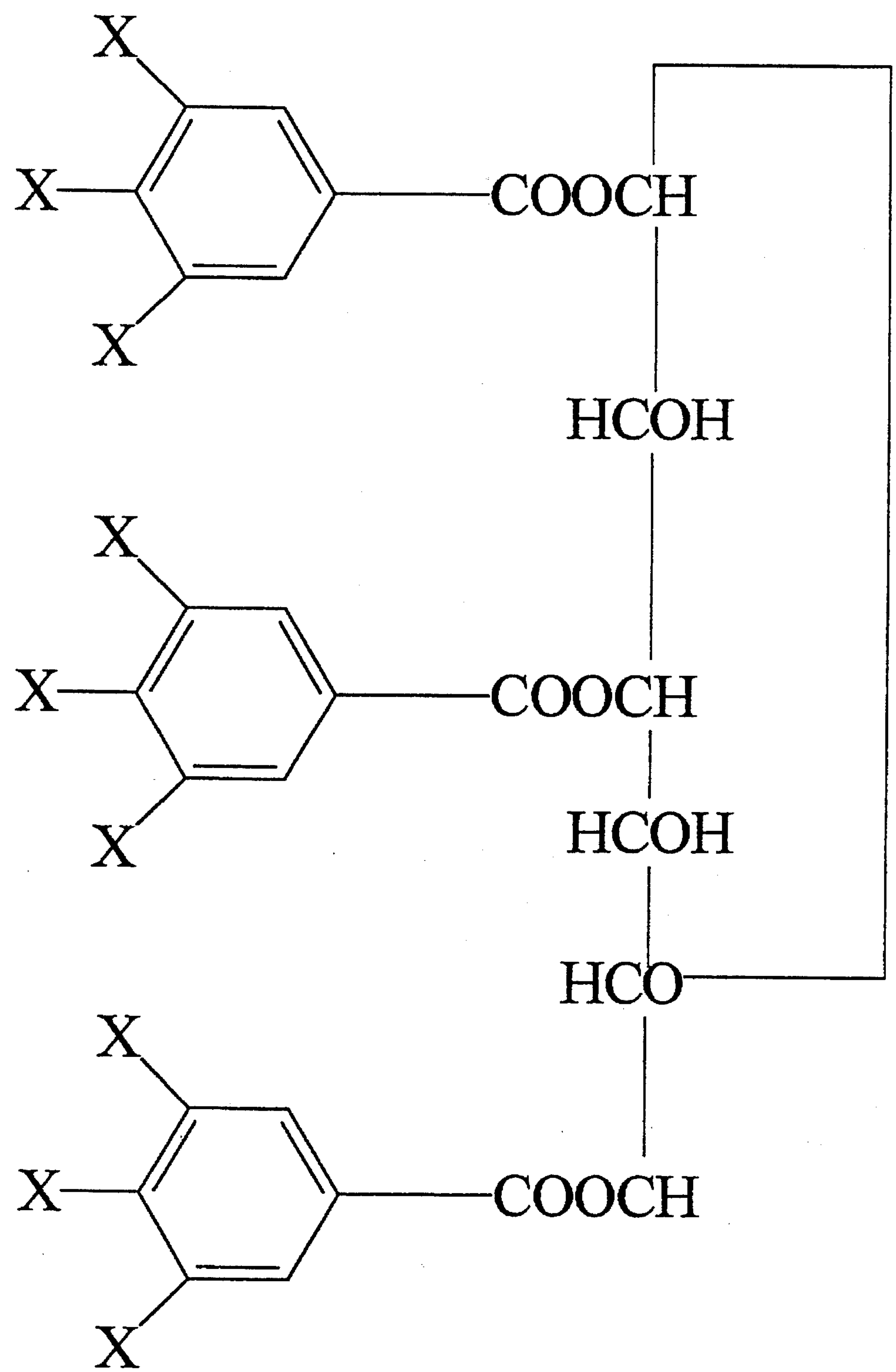
FIG. 1 is the general chemical formula for tannins. X can be independently selected from H, OH, anionic elements or compounds, or R, wherein R is a branched or unbranched carbon chain of 1–20 carbons.
Figure 2:
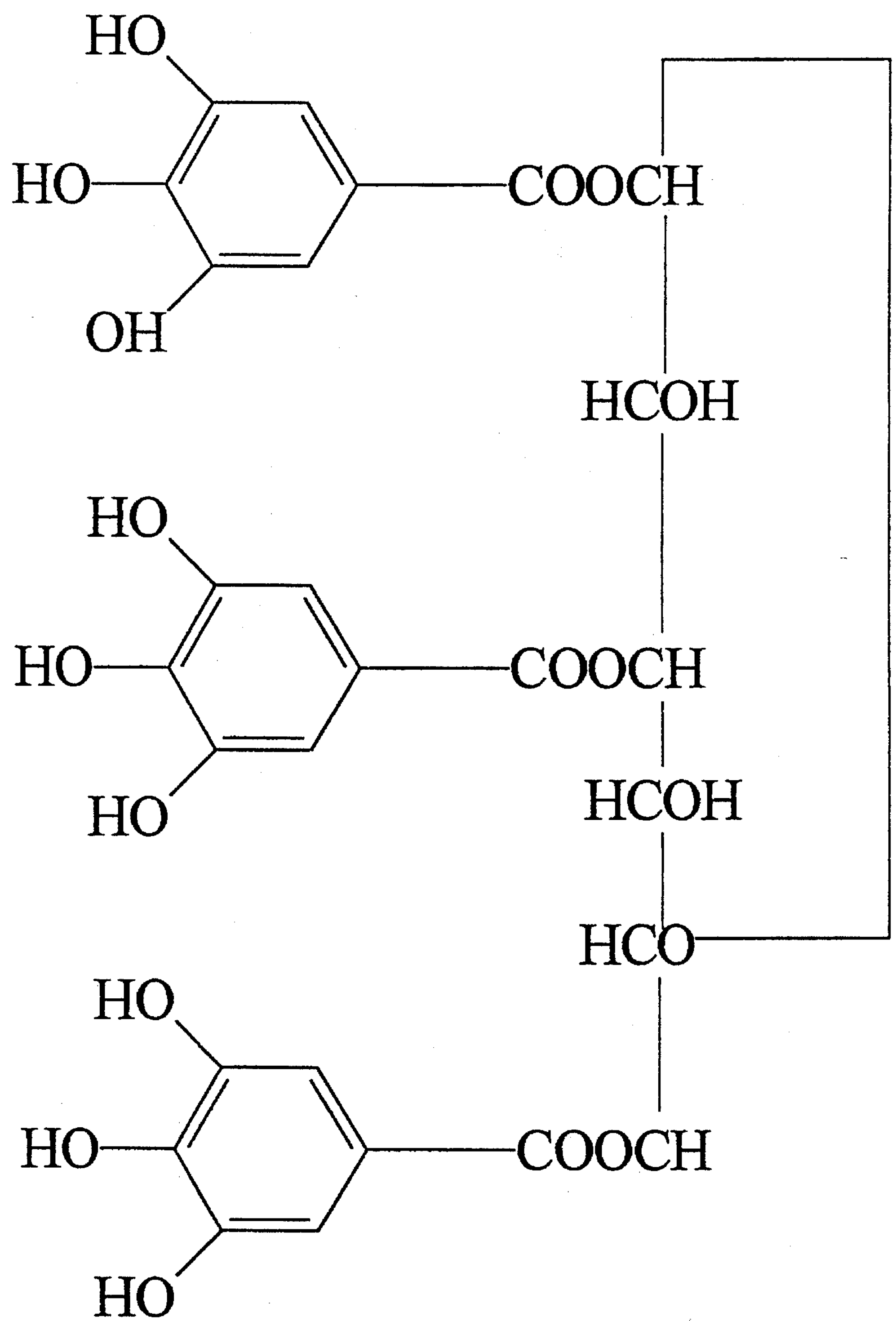
FIG. 2 is the chemical formula for tannic acid.
Figure 3:
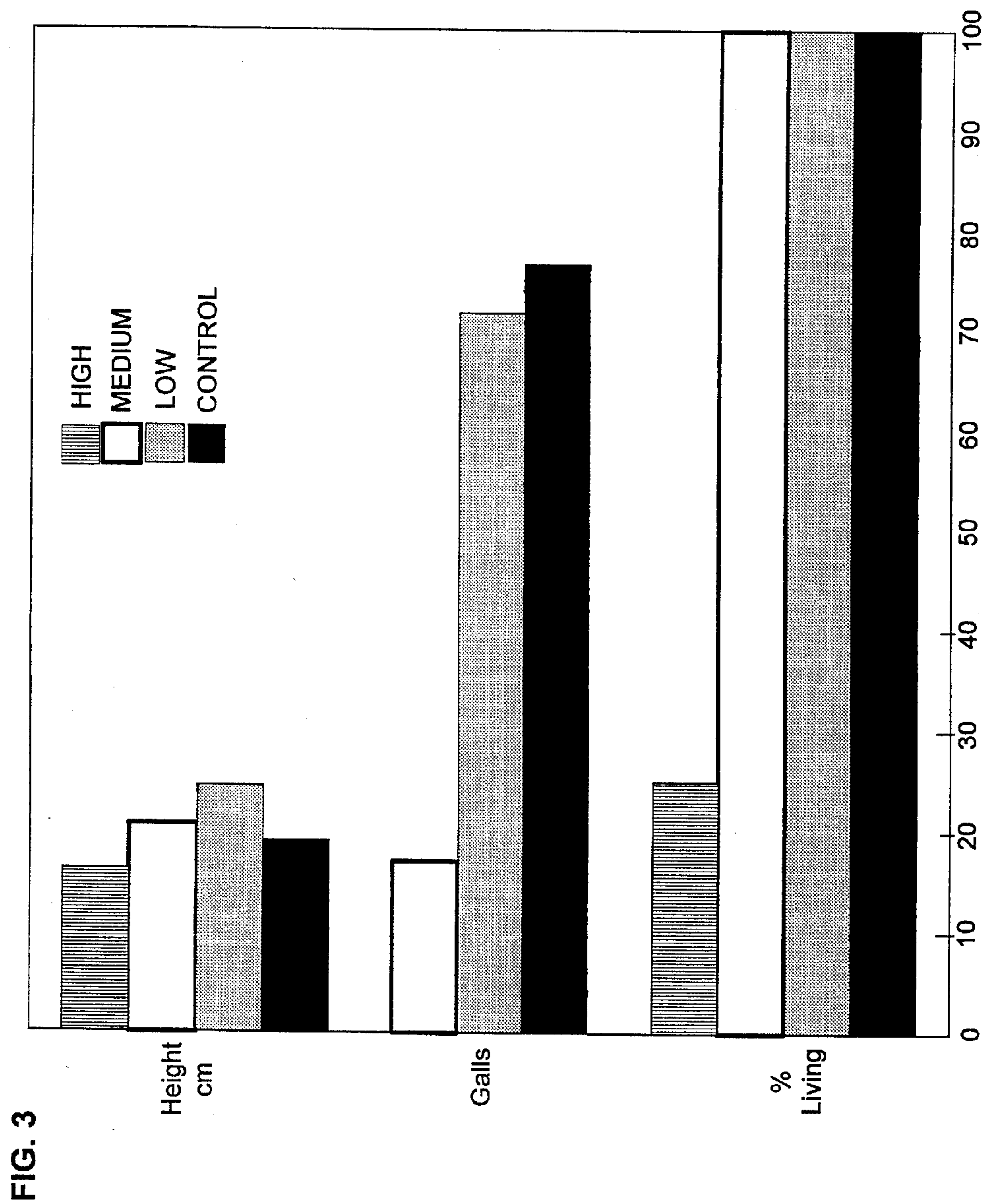
FIG. 3 shows the relationship between tannin concentration, the plant viability, the number of galls observed on the plant roots, and the plant height.

Many tannins and tannin derivatives can be useful to attract or kill nematodes according to the subject invention. As used herein, "tannins" include tannic acid and other condensed or hydrosaluable congeners, analogues, derivatives, and salts thereof. Preferably, the tannins used according to the subject invention will be hydrosaluable. Tannins used for the subject invention are commercially available, but can be extracted from bark, nuts, and other plant material or can be synthesized. The general structure of the tannins is shown in FIG. 1. Tannic acid has the general molecular formula of $C_{14}H_{10}O_9$. The structure for tannic acid is shown in FIG. 2. Tannic acid has been shown to be particularly effective in controlling nematodes. Various other tannin-derivatives, such as the precursors or break-down products of tannins, can also be used to attract and control nematodes.

Various pest-control compositions of the subject invention can be made according to known methods and techniques. The pest-control compositions of the subject invention may vary in the form in which they are produced and applied. Similarly, the pest-control compositions can vary in their chemical composition, most importantly in the concentration of tannin that is present. In addition, tannins can be used in a variety of ways to control nematodes. One skilled in the art will be able to optimize the efficacy of the subject invention for a desired application. For example, a certain range of tannin concentrations will be desirable for certain forms of application. Selecting the best concentration of tannin and the form of application will depend on the intended use of the subject invention, and will be readily recognized by ordinarily skilled artisans have the benefit of the teachings provided herein.

The effect of tannins on nematodes can vary with the tannin concentration. It has been found that in higher concentrations, e.g., soil concentrations of about 10,000 ppm or more, tannins are nematicidal. In one embodiment, tannins can be used at lower concentrations as a nemastat or nematode attractant. In this manner, applied tannins can be used to lead nematodes away from the desired plants. Advantageously, a natural concentration gradient of tannins forms radially around a point source of a pest-control composition comprising tannins (decreasing concentration at further distances from the point source). Nematodes can detect in soil the presence of tannins at concentrations of about 100 ppm or less. The effect on nematode locomotion, or normal search behavior is to attract the nematodes to higher concentrations of tannins. The concentration nearer the point source of the composition can be such that movement or activity is inhibited, immobilizing the nematodes so that plant damage can be prevented. Tannin concentration at the point source can be at high enough concentrations to kill the nematodes.

Thus, in one embodiment of the subject invention, tannins can be used in concentrations that attract nematodes. In this manner, various uses are possible. Tannins may be applied before planting seed ("pre-plant") or at the time in which seeds are planted ("at plant"), or when plants are already growing ("post-plant"). Thus, applied tannins are used to confuse nematodes by leading them away from the desired plants. This application greatly reduces the numbers of nematodes that are able to locate and parasitize plant root systems. In addition, tannins can be used to treat fields in order to stimulate nematodes to move during periods when crops are not present. Thus, nematodes use up their energy stores, become weakened, and die off. This is one embodiment in which the use of pest-control compositions of the subject invention are used as a preventive measure.

In another embodiment of the subject invention, the attractive nature of tannins is advantageously used in combination with other biological control agents. Tannins are used to lure nematodes to locations having chemical, biological, or other control agents, such as chemical pesticides or antagonistic biologicals, e.g., fungi and bacteria. Effective nematicidal concentrations of tannins can also be used. Various biological control agents have been described in the prior art. See, e.g. U.S. Pat. No. 4,948,734, Edwards et al., *Novel Isolates of Bacillus thuringiensis Having Activity Against Nematodes;* U.S. Pat. No. 5,151,363, Payne, *Isolates of Bacillus thuringiensis That Are Active Against Nematodes* which are hereby incorporated by reference. In one embodiment the tannins may be formulated with the second control agent or applied sequentially with the second control agent. In another embodiment traps may be used. Point-source traps can make use of a variety of different housings or containers that are also known in the art. Used in this manner, tannins may be used to decrease the amount of chemical or biological control agents needed to treat large field areas. This embodiment, as with other embodiments described herein, may be used to either control an existing nematode infestation or to prevent an infestation from occurring.

Relatively low rates of tannic acid in soft, e.g., less than about 10,000 ppm, have been observed to result in excellent control of nematodes. When inoculated on water agar, nematodes leave a distinct pattern as they move in search of food. The term "search behavior" refers to the natural foraging behavior of nematodes. In the presence of tannins at concentrations of about 100–10,000 ppm search behavior is stimulated and the patterns on water agar reflect increased foraging activity. At still higher concentrations, e.g., more than about 10,000 ppm, normal search behavior can be interrupted, the nematodes can exhibit immobilization, or "shock behavior". Complete shock behavior has been observed at tannin concentrations of about 30,000 ppm. Additional experiments have shown that nematodes will move up a tannin gradient until they begin shock behavior at which point they are unable to move any further up or down the gradient.

Where it is desired to administer the compositions of the subject invention in a dry, solid unit form, capsules, pellets, boluses, or tablets containing the desired amount of active compound are usually employed. The pellet, capsule, or boluses comprise the tannin, or tannins, mixed with appropriate, agriculturally acceptable carriers. These embodiments can be prepared by intimately and uniformly mixing the active ingredient with suitable finely divided diluents, fillers, disintegrating agents and/or binders. Such unit formulations may be varied widely with respect to their total weight and content of the antiparasitic agent, depending upon the factors such as the type of plants and soil to be treated, and the severity and type of infection.

The tannin compositions may also be administered as a liquid drench. The drench is normally a solution, suspension or dispersion of the active ingredient, usually in water, together with a suspending agents, wetting agents, or other suitable additives. The drenches may contain an anti-foaming agent. The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients can include various agents, surfactants, emulsifiers, dispersants, or polymers. Drench formulations may also be employed to apply the subject compositions along with other solutions that are typically applied to plants or fields, such as fertilizers or other insecticides. A preferred application method is drip irrigation under plastic mulch.

The tannin concentration in the pest-control compositions may be varied. Selection of the tannin concentration in the pest-control composition will depend on the nature of the particular formulation, particularly whether it is a concentrate or to be used directly, and on the precise nature of the area to be treated. In addition, an ordinarily skilled artisan would be able to adapt concentrations and formulations for the particular species of nematode to be controlled. The tannin will be present in an amount that will produce the desired concentration in the area to be treated. The skilled artisan will be able to determine the desired final concentration in, for example, the soil or a biological-control trap. The concentration of tannins in the application composition will be adjusted accordingly, as would be known by one skilled in the art. For example, for the control of nematodes according to the subject invention, tannins can be applied to the soil such that the concentration in the soil is an effective amount. As an effective attractant, tannin concentrations in the soil are preferably less than about 10,000 ppm. More preferably, the concentrations of the tannins for use as a nematode attractant is between about 100 ppm and about 10,000 ppm. Most preferably, the concentration is between about 5,000 and about 10,000 ppm for use as an attractant. Pesticidal activity can be effected at soil concentrations of more than about 10,000 ppm. Preferably, the soil concentration of tannins for use as a pesticidal composite is between about 10,000 ppm and about 100,000. More preferably the pesticidal composition is between about 25,000 and about 75,000 ppm, and most preferably between about 25,000 and about 50,000 ppm.

Tannins can be used to control nematodes in various settings, including farmland, golf courses, green houses, in the potted-plant industry, and around the home. The formulations discussed above can be applied to the environment of the nematodes, e.g., plants, soil or water, by spraying, dusting, sprinkling, or the like, in various manners that a skilled artisan would know are suitable.

Tannins are presently demonstrated to have activity against the many types of nematodes. The plant-parasitic nematodes that are the target of the present invention are members of the Phylum Nematoda. Nematodes that can be controlled by the subject invention belong to the Orders Tylenchida and Dorylaimide. In the Order Tylenchida, the plant-parasitic nematodes are found in two Super Families: Tylenchoidea and Criconematoidea. As set forth herein, tests were conducted on six different plant-parasitic nematode species. Five of the tested species are members of the Tylenchoidea group and the other is from the Criconematoidea group. Successful experimental data was obtained for each of the groups tested.

The skilled artisan would recognize that the present invention has far-reaching implications. The skilled artisan would recognize that various techniques are known in the art that may be used to optimize the practice of the subject invention. For example, screening plants for resistance to tannins may be useful. Thus, where the concentration of tannin necessary for the control (attraction or killing) of nematodes in a particular application is above the level that is normally toxic to typical varieties of the desired plant, resistant plants are useful. Resistant plants may be developed by simple screening techniques, by induced mutation and screening techniques, by breeding techniques, by genetic manipulation, and other techniques that are known in the art. Other advanced techniques may also be used, and are deemed to be within the scope of this invention. For example, as discussed above, the production of tannins and related intermediates can be catalyzed by various enzymes.

Recombinant DNA technology may be used to develop a recombinant cell, e.g., microorganisms or plants that would employ the necessary enzymes for the production and delivery of tannins. For example, certain bacterial species are know to produce metabolic products that are encapsulated in spore-like bodies. Such bacteria may be used to produce tannins. These tannin-containing bacteria may then be attenuated and applied directly to the fields. In addition, a large number of microorganisms are known to inhabit the soil. These microorganisms include bacteria, algae, and fungi. Thus, such microorganisms can be developed that would produce adequate levels of tannins; these microorganisms can then be applied, alive or dead, to the soft. Various applications of the discoveries set forth herein are considered to be within the scope of the invention.

In yet another embodiment plants having low levels of tannins are obtained through standard breeding techniques or via genetic manipulations. These plants, according to the subject invention are less attractive to nematodes and, thus, less susceptible to nematode infestation.

Following are examples which illustrate procedures, including the best mode, for practicing the invention. These examples should not be construed as limiting. All percentages are by weight and all solvent mixture proportions are by volume unless otherwise noted.

EXAMPLE 1

Nematode Mortality to Tannic Acid

Nematode mortality to tannic acid (commercially available [Fisher Scientific Co.]) was tested in small wells in which 10%, 1%, 0.1%, 0.01%, and 0% tannic acid solutions were placed, along with live root-knot nematode juveniles. After 24 hours, the 10% (100,000 ppm) solution killed all the nematodes, and the 1% (10,000 ppm) solution killed 50% of the nematodes. The 0.1% and 0.01% solutions were not observed to be different than the water control.

EXAMPLE 2

Penetration of Root Systems by Root-Knot Nematodes

The ability of root-knot nematodes to penetrate root systems was tested using the same techniques as in Example 1, except the 0.01% solution was not used. After 24 hours, nematodes were extracted from the tannic acid solutions, placed into clean water, and then inoculated onto tomato plants. Nematodes soaked in the 10% solution did not penetrate the roots. Nematodes from the 1% solution produced an average of 0.2 galls per root system. Galls are bodies that are observable on a nematode-infected root. Root penetration by nematodes soaked in the 0.1% solution averaged 46.4 galls per root system. The water control had an average of 36.4 galls per root system. It is believed that the 0.1% solution did not result in a significant difference from the control.

EXAMPLE 3

Nematode Attraction to Tannic Acid

Nematode attraction to tannic acid was demonstrated using petri dishes filled with water agar. A well was cut in the center of the petri plate by removing a 1.5 cm circular piece of water agar. 10%, 1% and 0.1% solutions of tannic acid and water control were placed in the center of the well. After 3 hours, root-knot nematodes were placed in petri plates and their behavior was observed. Their behavior was determined by observing the nematodes and their tracks left on the agar. Behavior was different in plates that contained a 10% solution. Nematodes made looping tracks, a normal search behavior that occurs when tannins are detected, at a regular distance from the tannic acid well. Those nematodes that had moved closer to the well performed a continuous shock behavior which is normally done for a short time when a nematode detects a chemical or physical gradient and changes direction to move up or down the gradient. Shock behavior is characterized by a loss of locomotion.

EXAMPLE 4

Additional Characterization of the Attraction

Attraction of nematodes to tannic acid was also demonstrated by using petri plates filled with 15 ml of water agar. For this experiment, Meliodoyne nematodes were used. Two 1.5 cm circular wells were cut out of the agar, using a test tube, at opposite ends of each petri plate. 0.3 ml of a 10% tannic acid solution was placed into one well and water was placed into the other well. In control petri plates, only water was added. After 48 hours, newly hatched juvenile nematodes in a 0.03 ml suspension were placed in the middle of the dish using a micropiper. After 24 hours, plates were observed and the position of the nematodes was marked on the lid. 91% of the nematodes were found to be in the zone around the wells containing tannic acid.

EXAMPLE 5

Nematode Movement Through Tannic Barriers

Nematode movement through a tannic acid barrier was tested using petri plates filled with water agar. A 1 cm strip of filter paper soaked in tannic acid was placed in the middle of each plate so that it touched both sides of the plate and delineated the diameter of the dish. The tannic acid was allowed to leach onto the plate from the filter paper. After four hours, the filter paper was removed. Nematodes placed on these plates were unable to cross the tannic acid barrier formed. The nematodes were attracted toward the tannic acid but did not move through and onto the other side. Thus, one embodiment of the subject invention is the creation of a tannin barrier around locations for which nematode protection is desired.

EXAMPLE 6

Ability of Nematodes to Detect Tannic Acid

The ability of root-knot nematodes to detect tannic acid was tested by placing tannic acid solutions of 10%, 1%, 0.1%, and 0% onto water agar. After three days, which allowed the agar to become saturated, nematodes were added, and their behavior was observed. On the control plates, no alteration in the nematodes behavior was observed. Juveniles began search behavior (looping tracks) at the lowest concentration of tannic solution tested (300 ppm). The search behavior became more intense on the plates treated with the 3,000 ppm tannic solution. At the highest concentration (30,000 ppm), nematodes were in what we term "complete shock behavior." In the state of complete shock behavior, nematodes are able to move their heads around, but they are unable to move from the point of initial inoculation.

EXAMPLE 7

Soil-Drenching Application Techniques

Soil application techniques were tested using 10 g, 1 g and 0.1 g rates of tannic acid, applied both preplant and at plant. Soil that had been inoculated with newly hatched root-knot nematodes was treated with tannic acid powder and tannic acid dissolved in water. The 10 g rate (approximately 20,000 ppm) killed all tomato plants. The 1 g rate (2,000 ppm), applied at plant, gave the best result. Those plants averaged 3.5 galls. The untreated control had an average of 63.2 galls per plant. The 0.1 g rate (200 ppm), applied preplant, had 44.2 galls per plant, which was not significantly different than the control.

EXAMPLE 8

Formation and Use of a Point-Source Attractant

An alternate method tested was the use of tannic acid pellets as a point-source attractant. Tannic acid was pelleted by mixing it with a solution of Gelcrin. This solution was dripped into a 10% potassium chloride solution which caused the encapsulation of the solution. The pellets were air dried. 2.5 g, 1 g, 0.5 g and 0.1 g of pellets were applied, at plant, to soil in pots. The 0.1 g, 0.5 g and 1 g had significantly lower numbers of galls (average of 4.5, 3.5, 8, respectively) than the control (average of 21 galls).

Another embodiment of the subject invention is the use of tannin to attract nematodes to a location wherein they can be counted. Thus, in this embodiment, tannins are used in a procedure for the detection and/or monitoring of nematode populations.

Use of the subject pest-control compositions and their methods of use would be readily recognized and adaptable by a person familiar with the use of a standard pest-control techniques for the protection of plants. The skilled artisan would recognize the significance of the present disclosure and, with routine experimentation and adaptation, could easily apply the above-described procedures for many large-scale applications.

Although the foregoing invention has been described in some detail by way of illustration and example, it will be understood that the present invention is not limited to the particular description and specific embodiments described, but rather may comprise a combination of the above elements and variations thereof, many of which will be obvious to those skilled in the art in view of this disclosure. It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for controlling migrating nematodes, said method comprising the steps of:

(a) applying a nematode-attracting amount of a tannin to a plant growth medium; and (b) attracting the nematode away from a desired plant, thereby preventing damage to the plant.

2. The method, according to claim 1, wherein said tannin concentration is between about 2,000 ppm and about 10,000.

3. The method, according to claim 1, wherein said tannin is administered the form of a point source.

4. The method, according to claim 1, wherein said tannin is administered as a liquid form.

5. The method, according to claim 1, wherein said tannin is administered as a solid form.

6. The method, according to claim 1, wherein said tannin is applied at a pro-planting stage.

7. The method, according to claim 1, wherein said tannin is applied at a planting stage.

8. The method, according to claim 1, wherein said tannin is applied at a post-planting stage.

9. The method, according to claim 1, wherein said method further comprises attracting said nematode to an agent lethal to a nematode.

* * * * *

UNITED STATES PATENT AND TRADEMARK OFFICE

CERTIFICATE OF CORRECTION

PATENT NO. : 5,595,748

DATED : January 21, 1997

INVENTOR(S) : Eric M. Hewlett and Thomas E. Hewlett

It is certified that error appears in the above-identified patent and that said Letters Patent is hereby corrected as shown below:

Column 1: line 21: "toms" should read --toxins--.
Column 2: line 29: "soft" should read --soil--.
Column 4: line 54: "soft" should read --soil--.
Column 6: line 45: "soft" should read --soil--.
Column 7: line 53: "micropiper" should read --micropipet--.

Column 10: line 2: Claim 38: "administered the form" should read --administered in the form--.
Column 10: line 8: Claim 41: "pro-planting" should read --pre-planting--.

Signed and Sealed this

Thirteenth Day of May, 1997

Attest:

BRUCE LEHMAN

*Attesting Officer* *Commissioner of Patents and Trademarks*